(12) United States Patent (10) Patent No.: US 9,291,589 B2
Wong et al. (45) Date of Patent: Mar. 22, 2016

(54) WEARABLE ARTICLES WITH WETNESS SENSING

(75) Inventors: Sun Hoi Wong, Shatin (HK); Fei Xu, Shatin (HK); Hao Huang, Shatin (HK)

(73) Assignee: Ckicom Technology Limited, Shatin, N.T. (HK)

( * ) Notice: Subject to any disclaimer, the term of this patent is extended or adjusted under 35 U.S.C. 154(b) by 0 days.

(21) Appl. No.: 13/581,534

(22) PCT Filed: Jan. 20, 2012

(86) PCT No.: PCT/IB2012/050271
§ 371 (c)(1),
(2), (4) Date: Aug. 28, 2012

(87) PCT Pub. No.: WO2012/114208
PCT Pub. Date: Aug. 30, 2012

(65) Prior Publication Data
US 2013/0324955 A1  Dec. 5, 2013

(30) Foreign Application Priority Data

Feb. 24, 2011 (CN) .................. 2011 1 10044265
Apr. 12, 2011 (CN) .................. 2011 1 10094407
Jul. 19, 2011 (CN) .................. 2011 1 10202777

(51) Int. Cl.
*A61F 13/15* (2006.01)
*G01N 27/22* (2006.01)
*A61F 13/42* (2006.01)

(52) U.S. Cl.
CPC .............. *G01N 27/223* (2013.01); *A61F 13/42* (2013.01); *A61F 2013/424* (2013.01)

(58) Field of Classification Search
CPC .............. A61F 13/42; A61F 2013/424; A61F 2013/425; A61F 2013/426
USPC ........................................................ 604/361
See application file for complete search history.

(56) References Cited

U.S. PATENT DOCUMENTS 5,291,181 A * 3/1994 DePonte .................... 340/573.6
5,760,694 A   6/1998 Nissim et al.
(Continued)

FOREIGN PATENT DOCUMENTS

CN          2454776 Y    10/2001
CN        101320009 A    12/2008
(Continued)

OTHER PUBLICATIONS

International Search Report—PCT/IB2012/050271, mailed on Jun. 14, 2012.
(Continued)

*Primary Examiner* — Lynne Anderson
(74) *Attorney, Agent, or Firm* — Nixon Peabody LLP; Jeffrey L. Costellia (57) ABSTRACT

A wearable article for wearing by a user and comprising wetness sensing electrodes, wherein the wetness sensing electrodes are to be in contact with a wetting electrolytic liquid during normal use when the wearable article is wetted by the electrolytic liquid, and to operate as a capacitor upon application of a direct current at contact terminals of the wetness sensing electrodes when so wetted to facilitate capacitance measurement through the wetness sensing electrodes whereby wetness information of the wearable article is provided.

20 Claims, 6 Drawing Sheets

(56) References Cited

U.S. PATENT DOCUMENTS

| | | | | |
|---|---|---|---|---|
| 5,790,036 | A | * | 8/1998 | Fisher et al. .................. 340/605 |
| 6,175,310 | B1 | * | 1/2001 | Gott .............................. 340/605 |
| 6,373,395 | B1 | * | 4/2002 | Kimsey ......................... 340/602 |
| 2008/0266117 | A1 | * | 10/2008 | Song et al. ................. 340/573.5 |
| 2008/0278337 | A1 | * | 11/2008 | Huang et al. ............... 340/573.5 |
| 2009/0326493 | A1 | * | 12/2009 | Wada et al. .................. 604/361 |
| 2010/0152688 | A1 | * | 6/2010 | Handwerker et al. ......... 604/361 |
| 2011/0263952 | A1 | * | 10/2011 | Bergman et al. .............. 600/309 |
| 2012/0323194 | A1 | * | 12/2012 | Suzuki et al. ................. 604/361 |

FOREIGN PATENT DOCUMENTS

| | | |
|---|---|---|
| CN | 01847514 A | 9/2010 |
| EP | 0351891 B1 | 9/1993 |
| JP | 2002-82080 A | 3/2002 |

OTHER PUBLICATIONS

Patent Examination Report No. 1 on Australian Patent Application No. 2012203498 by IP Australia mailed on Aug. 30, 2013.

* cited by examiner

WEARABLE ARTICLES WITH WETNESS SENSING

FIELD OF INVENTION

The present invention relates to wearable articles with wetness sensing devices, and more particularly, to diapers having wetness sensing electrodes. This invention also relates to electrolyte level detection.

BACKGROUND OF INVENTION

Wearable articles such as diapers having wetness sensing are useful to provide wetness information for use or for reference by service or medical personnel. For example, diapers having electronic wetness sensing are useful to health care professionals because the wetness state of a diaper can be determined without actual diaper inspection. The availability of diapers having electronic wetness sensing arrangements has drastically improved the quality of life of bed-confined patients or the elderly having mobility problems.

Wetness detection in wearable article is typically facilitated by way of resistance or capacitance measurements. To facilitate wetness detection, wetness sensing electrodes are usually formed on the wearable article and the instantaneous capacitance or resistance values across the electrodes are then measured to determine the wetness of such a wearable article. However, conventional wetness detection systems only provide very raw information on whether a wearable article has been wetted, but are unable to provide more precise or detailed wetness information such as the level, degree or specific location of wetness.

Conventional wetness detection in wearable articles using the resistance detection approach has known shortcomings, such as, for example, unable to provide information on the extent of wetness. On the other hand, conventional wetness detection using capacitance detection is prone to external interference due to the small capacitance across the electrodes, because the capacitance across the electrodes is typically in the region of several picofarads. Furthermore, measurement of such a small capacitance means the need of a high frequency oscillation circuitry which adds to detection circuit complexity and is vulnerability to interference. Similar shortcomings are also present in conventional electrolyte level detection systems using resistance or capacitance measurements, and anode oxidation is a known problem.

SUMMARY OF INVENTION

Accordingly, there is provided a wearable article for wearing by a user and comprising wetness sensing electrodes, wherein the wetness sensing electrodes are to be in contact with a wetting electrolytic liquid during normal use when the wearable article is wetted by the electrolytic liquid, and to operate as a capacitor upon application of a direct current at contact terminals of the wetness sensing electrodes when so wetted to facilitate capacitance measurement through the wetness sensing electrodes whereby wetness information of the wearable article is provided. Electrodes which operate as a capacitor upon application of a direct current when in the presence of an electrolytic liquid are known to have characteristic capacitance values within the microfarad range and are therefore more suitable for wetness detection.

In an example, the wearable article is a diaper defining a groin region and a hip region and the wetness sensing electrodes provide an interface for incontinence management. The wetness sensing electrodes may comprise a first elongate electrode and a second elongate electrode which extends alongside the first elongate electrode. The wetness sensing electrodes may be printed of carbon ink. The carbon ink electrode may be printed on an elongate polyethylene film.

In another embodiment, the wetness sensing electrodes is adapted to operate as a capacitor having an electric double layer, otherwise known as a super capacitor, when wetted by an electrolytic liquid such as urine and when in use for wetness sensing.

For example, at least one of the wetness sensing electrodes may be a strip metal electrode which is covered with an insulating metal oxide of a high dielectric constant, and wherein the capacitance between the electrodes is determined by the wetted surface area of the electrode which is covered with the insulating metal oxide, the thickness and dielectric constant of the insulating oxide.

In an example, at least one of the wetness sensing electrodes comprises a strip metal electrode, the strip metal electrode comprising aluminum or tantalum which is covered respectively with aluminum oxide or tantalum oxide as an insulating dielectric layer.

The insulating oxide layer may have a thickness of more than 2 nanometers, and preferably up to 20 nanometers.

In this embodiment, at least one of the wetness sensing electrodes comprises a strip electrode of nano-porous material, and wherein the nano-porous strip electrode is adapted to from an electric double layer when in use for wetness sensing.

In another aspect, there is provided a wetness evaluation device suitable for use with the wearable article as disclosed herein, wherein the device comprises wetness detection circuitry for measuring capacitance or variation of capacitance between the wetness sensing electrodes by applying a direct current.

The device may further comprise means for measuring resistance or variation on resistance of the wetness sensing electrodes to provide location specific wetness information.

In yet another aspect, there is provided an electrolytic level detecting device comprising a first electrode, a second electrode and detection circuitry, wherein the first and second electrodes are adapted to be immersed in an electrolyte the level of which is to be detected, and the detection device is adapted to facilitate measurement of capacitance between the first and second electrodes to provide level information by direct current. In one example, at least one discrete wetness level marker is formed on at least one of the electrodes to provide a discrete indication on the level of the electrolyte. In another example, a plurality of discrete wetness level marker is formed on at least one of the electrodes to provide indication on discrete levels of wetness of the electrolyte. The wetness marker may be a capacitive mask which generates a shoulder portion of a local plateau in a capacitance versus wetness level relationship.

BRIEF DESCRIPTION OF DRAWINGS

Examples of the present invention will be illustrated by way of example with reference to the accompanying drawings, in which:—

DETAILED DESCRIPTION OF EXAMPLES

Figure 1:
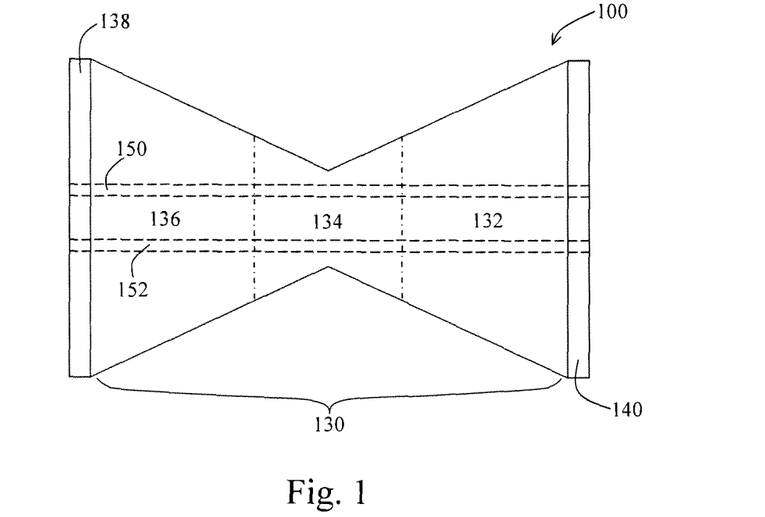
FIGS. 1 and 1A are schematic diagrams respectively depicting a plan view of an inner surface and a longitudinal cross-sectional view of a first example wearable article according to the present disclosure.

A diaper 100 shown schematically in FIG. 1, as an example of a wearable article, comprises a flexible diaper body 120, a first electrode 150, and a second electrode 152. The flexible diaper body 120 comprises a liquid-permeable inner layer 122, a liquid impermeable outer layer 124 and a liquid absorbent layer 126 which is intermediate the inner and outer layers. The inner layer 122 is made of a non-allergic liquid permeable or hydrophilic material such as a non-woven fabric made from fibers of rayon, acetate, cotton pulp, or synthetic resin. This inner layer 122 includes an inner surface 130 which is adapted to be worn in abutment with the skin of a user during use to separate the skin of a user from direct contact with the underlying wetted absorbent layer 126 during use. The outer layer 124 is made of a liquid non-permeable material such as a sheet of synthetic resin film. The outer layer 124 is water proof or substantially water proof to mitigate or prevent liquid leakage from the diaper 100. The absorbent layer 126 is adapted to collect and retain urine or other body liquid which enters the absorbent layer 126 after passing through the inner layer 122. The absorbent layer 126 is usually made of pulp, rayon, acetate, natural cotton, super absorbent polymer, synthetic fibers, or a combination or mixture thereof. The absorbent layer 126 has a typical thickness of about 0.5 cm to 1 cm, or even 1.5 cm, and is usually filled with fluffy urine or liquid absorbent fillings.

The inner surface 130 of the flexible diaper body primarily comprises 3 main regions, namely, a groin region 136, a crotch region 134 and a hip region 132, which are distributed along a longitudinal direction, with the crotch region 134 intermediate the hip and groin regions 132, 136. It will be appreciated that the longitudinal direction would be the direction which is parallel or substantially parallel to the body axis of a user during use. Each of the hip and groin regions has a laterally extending waist mount portion at a longitudinal end which is an end distal from the crotch region. The waist mount portions 138, 140 respectively of the groin and hip regions meet and engage with each other during use when worn by a user and collectively form a tensioned waist mount surrounding the waist of the user.

Each of the hip and groin regions tapers towards the crotch region from the respective waist mount portions 138, 140 to form a narrowed crotch region 134 at the middle of the diaper body 100. The crotch region 134 is the narrowest portion of the diaper body 100 and is adapted to be fitted between the thighs of a user and forms the lowest urine collection portion of the diaper during use. In addition, the hip and groin regions 132, 136 are substantially symmetrical about the crotch region 134.

Figure 1A:
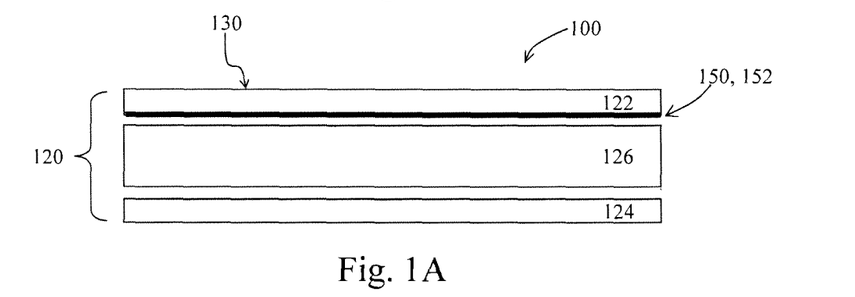

In a first diaper example as shown in FIGS. 1, and 1A, a first electrode 150 and a second electrode 152 are both formed on the inner hydrophilic layer 122 of the diaper body 100 by attaching to the underside of the inner hydrophilic layer 122 so that the active electrode surfaces are in direct or contiguous contact with the absorbent layer 126 which is immediately underneath the hydrophilic layer 122. The electrodes run parallel or substantially parallel to each other and extend side by side along the longitudinal direction on the same inner surface 130 of the diaper body 100. Each of the first 150 and the second 152 electrodes is elongate and extends from the groin region 136 of the diaper 100 to the hip region 132 of the diaper 100 at the rear. The electrodes 150, 152 terminate at the waist mount portions 138, 140 and expose at at least one longitudinal end of the diaper body 100 to form contact terminals. The contact terminals facilitate making of electrical connections with an external wetness detection device so that wetness data can be passed from the diaper 100 to the external wetness detection device.

The electrodes 150, 152 and the absorbent layer 126 collectively form a wetness sensor arrangement for detecting the wetness state of the diaper 100. Specifically, the first and second electrodes 150, 152 are wetness sensing electrodes which are adapted to be in direct contact with the wetting liquid (e.g. urine) trapped by the absorbent layer 126 during use when the diaper 100 is wetted. The electrodes 150, 152 and the absorbent layer 126 is adapted such that the wetness sensor comprising the electrodes 150, 152 and the wetted absorbent layer 126 is primarily a capacitive sensor having capacitance properties or behavior of an electrochemical capacitor such as an electrolytic capacitor or super capacitor. The capacitive characteristics of an electrochemical capacitor are desirable because a high capacitance value can be obtained by electrodes of a relatively small volume, such as strip or film electrodes suitable for use on a diaper.

In a first example, each of the first and second electrodes 150, 152 is printed of a conductive ink such as carbon ink, and the conductive ink is printed on an elongate polyethylene (PE) base film. Each of the first and second electrodes 150, 152 has a length of 90 cm and a width of 0.8 cm with a total series resistance of 100 kΩ. The total capacitance measured across the entire length of the first and second electrodes 150, 152 when both are wetted are in the region of 200 μF. It will be understood by persons skilled in the art the length and width of the electrodes can be adjusted according to the variation in diaper size. In general, the electrodes will have a length of more than 250 mm and a width of more than 2 mm. It will be appreciated that the electrodes of the diaper when immersed in urine operate similar to the principle and structure of a super capacitor upon application of a direct current.

In a second example, each of the first and second electrodes 150, 152 is an elongate aluminum foil strip having a width of about 0.8 cm and a length of about 90 cm extending along the longitudinal direction for a medium size diaper. The aluminum strips of the first and second electrodes 150, 152 have a lateral (side by side) separation of about 0.8 cm and are adhered on the underside of the inner layer 122 such that the aluminum strips are intermediate the inner layer 122 and the absorbent layer 126 to permit immersion by urine or other body liquid when the crotch portion 134 of the diaper 100 is wetted. The first electrode 150 is adapted to be the anode and is coated with an aluminum oxide as an example of an insulating oxide layer. Aluminum oxide has a dielectric constant of about 10 and can withstand an electric field strength of 1 volt per 1.2 nanometer, or more than 800 volt per micrometer (800 V/μm). An aluminum oxide layer having a thickness of more than 2 nanometers would be sufficient for the present application. The aluminium oxide layer thickness may be up to 20 nanometers. The oxide insulating layer on Aluminum is usually formed by an anodizing process. As naturally occurring Aluminum has an oxide film which can withstand a voltage of about 1.5 volt, aluminum electrodes can be readily used for this application without dedicated surface processing. Tantalum is another substance of similar capacitive properties which is suitable for use as wetness sensing electrodes without loss of generality. Both aluminum and tantalum based wetness sensors for diapers have a similar range of capacitance. The aluminum or tantalum based wetness sensor has a typical capacitance value in the microfarad (μF) region, which is far greater than the picofarad (pF) region of conventional wetness sensor of diapers. In general, the aluminum electrode based wetness sensor has a typical capacitance value between 1 μF and 100 μF on wetted absorbent layer. It will be appreciated that the electrodes when immersed in urine and subject to a direct current will operate similar to the structure and operation of an electrolytic capacitor.

Wetness sensing electrodes having the properties of an electrolytic capacitor are preferred because the capacitance of an electrolytic capacitor is largely determined by the surface area of electrodes and the associated high dielectric oxide layer thickness. This characteristic makes possible a larger capacitance value in strip electrode form which is particularly suitable for diaper or clothing applications.

In other electrode embodiments, substances suitable for forming electric double layer capacitor ('ELDC') or supercapacitors are employed to form the wetness sensing electrodes. Such substances include, for example, pure carbon, activated carbon, carbon composite, carbon fiber composite, graphite, graphene, carbon nano-tube, carbonized ink, conductive rubber, metal oxides, aqueous synthetic substances, metal composite, conductive polymers. In these embodiments, the electrodes and the wetted absorbent layer collectively formed a super-capacitor having a very large capacitance in a very small volume.

To maintain the electrodes in position on the diapers and to maintain a separation between them, the carbon electrodes or other flexible electrodes such as ELDC electrodes are first fixed on a hydrophilic film such as a polymeric film of a high polymer number like PVA film, and then attached as a modular attachment to the diaper.

It is noted that ELDC based wetness sensing electrodes, such as conductive ink based wetness sensors, have a typical capacitance value in the microfarad (μF) region, which is far greater than the picofarad (pF) capacitance of conventional wetness sensor of diapers. In general, the printed conductive ink based wetness sensor has a typical capacitance value between 100 μF and 600 μF on a urine wetted absorbent layer. Such a capacitance range provides a good balance between measurement speed and resistance to interference, since an exceedingly high capacitance value will result in a slow measurement time.

In use, the capacitance of the wetted diaper is measured, for example, by measuring the rate of change of voltage across the electrodes by applying a constant current. The degree of wetness can be evaluated by the wetness evaluation circuitry as the capacitance of the diaper across the first and second electrodes increases with an increase in wetted area.

Figure 2:
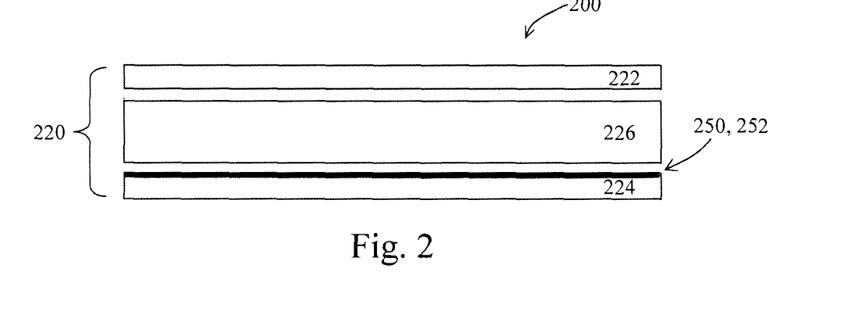
FIG. 2 is a schematic diagram depicting a longitudinal cross-sectional view of a second example diaper according to the present disclosure.

In a second example diaper 200 as shown in FIG. 2, a first electrode 250 and a second electrode 252 are both formed on the inner, user facing, surface of the outer water proof layer 224 of the diaper body 200. More particularly, the electrodes 250, 252 are placed immediately underneath the absorbent layer 226 and immediately above the leakage proof layer 224. The electrodes 250, 252 run parallel or substantially parallel to each other and extend side by side along the longitudinal direction on the same inner surface of the diaper body 200. The first and second electrodes 250, 252 terminate at the waist mount portions and are exposed at at least one longitudinal end of the diaper body 200 to facilitate the making of electrical connections with an external wetness detection device. As parts of the second example diaper are materially identical to that of the first example, parts which are of the same or equivalent function are represented by the same numerals plus 100.

Figure 3:
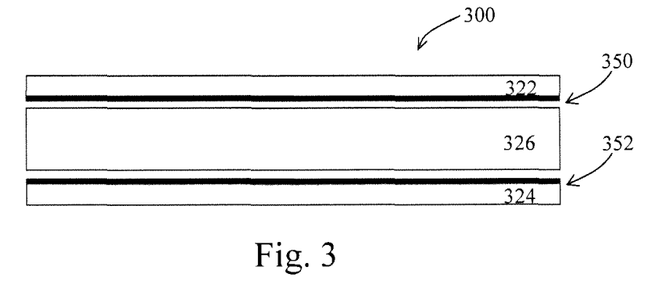
FIG. 3 is a schematic diagram depicting a longitudinal cross-sectional view of a third example diaper according to the present disclosure.

In a third example diaper 300 as shown in FIG. 3, a first electrode 350 and a second electrode 352 run in parallel or substantially parallel to each other and extend along the length of the diaper body 300 along the longitudinal direction. The electrodes 350, 352 are disposed in a substantially overlapping manner with the absorbent layer 326 of the diaper body 300 intermediate the first electrode 350 and a second electrode 352. The electrode 350 is fixed onto the underside of the inner layer 322. The electrodes 350, 352 are adapted to be in direct contact with the absorbent layer 326 and therefore urine collected therein when the absorbent layer 326 is wetted during use. The first and second electrodes 350, 352 terminate at the waist mount portions and are exposed at at least one longitudinal end of the diaper body 300 to facilitate the making of electrical connection with an external wetness detection device. As parts of the third example diaper are materially identical to that of the first example, parts which are of the same or equivalent function are represented by the same numerals plus 200.

Figure 4:
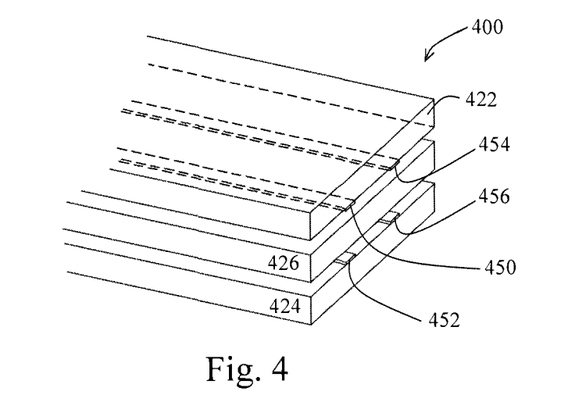
FIG. 4 is a schematic perspective view depicting a longitudinal cross-sectional view of a fourth example diaper according to the present disclosure

In a fourth example diaper 400 as shown in FIG. 4, a first electrode 450 and a second electrode 452 run in parallel or substantially parallel to each other and extend along the length of the diaper body 400 along the longitudinal direction. The first and second electrodes 450, 452 are disposed in a substantially overlapping manner with the absorbent layer 426 of the diaper body 400 intermediate the first electrode 450 and a second electrode 452. In addition, a third electrode 454 and a fourth electrode 456 run in parallel or substantially parallel to each other and extends along the length of the diaper body along the longitudinal direction. The third and fourth electrodes 454, 456 are also disposed in a substantially overlapping manner with the absorbent layer 426 of the diaper body intermediate the third electrode 454 and the fourth electrode 456. Furthermore, the first and third electrodes 450, 454 are disposed in adjacent on the same inner facing surface while the second and fourth electrodes 452, 456 are disposed in adjacent on the same inner surface of the water proof outer layer 424. The four electrodes are adapted to be in direct contact with the absorbent layer 426 and therefore urine collected therein when the absorbent layer 426 is wetted during use. The four electrodes terminate at the waist mount portions and are exposed at at least one longitudinal end of the diaper body 400 to facilitate the making of connections with an external wetness detection device. As parts of the fourth example diaper are materially identical to that of the first example, parts which are of the same or equivalent function are represented by the same numerals plus 300.

As the inner layer 122 will be the layer which is in direct contact with or is proximal with the skin of a user during normal use, disposing capacitor forming electrodes on the inner layer would facilitate detection of urine immediately upon occurrence of incontinence. On the other hand, capacitor forming electrodes disposed on the outer layer 124 will provide useful indication on the severity of wetness since a substantial increase in capacitance between the capacitor forming electrodes disposed on the outer layer 124 would mean that urine has passed through the absorbent layer 126. Therefore, it is advantageous to dispose capacitor forming electrodes on different layers of the diaper since useful information on the extent of wetness can be compiled with reference to the variation in capacitance values on the capacitor forming electrodes disposed on the inner layer 122 and the outer layer 126.

Figure 5:
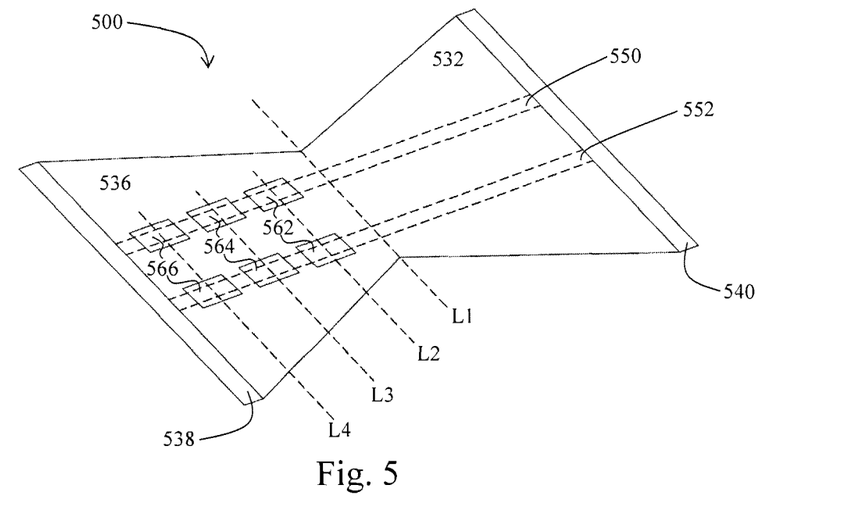
FIG. 5 is a schematic diagram depicting a plan view of an inner surface of a fifth example diaper according to the present disclosure.
Figure 5A:
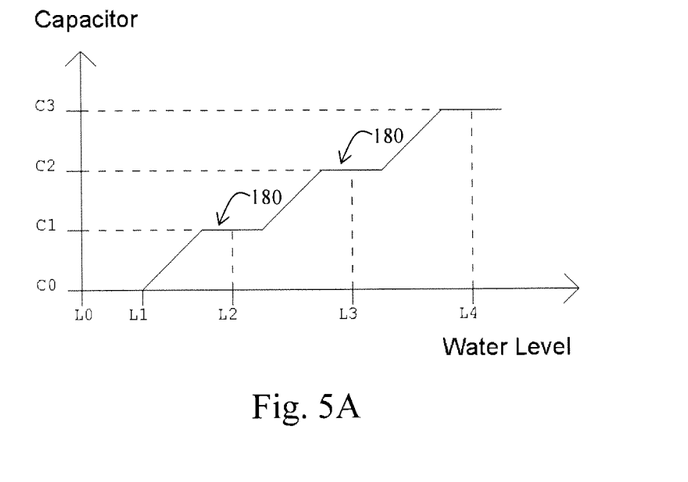
FIG. 5A is a schematic diagram illustrating exemplary characteristics of variation of capacitance with respect to the level of wetness of the diaper of FIG. 5 during use.

In a fifth example diaper 500 as schematically shown in FIG. 5, a first electrode 550 and a second electrode 552 run in parallel or substantially parallel to each other and extend along the length of the diaper body 500 along the longitudinal direction similar to diapers of the first and the second examples. Three sets of markers 562, 564, 566 as an example of a plurality of level markers are distributed along the length of each of the electrodes 550, 552 and spaced apart. The markers of the electrodes are distributed such that corresponding markers on the first and second electrodes are representative of the same wetness level during use. Each marker comprises a capacitance mask which retards the increase of capacitance with increasing wetness, thereby creating a capacitance shoulder region 180 as shown in FIG. 5A. More specifically, the first 562, second 564 and third 566 markers are adapted to correspond to levels L2, L3, and L4 respectively when the diaper is worn, with L1 correspond to the lowest level.

Each marker on an electrode comprises a lengthwise portion of waterproof insulation layer covering a lengthwise portion of the electrode. The insulation layer diminishes the additional capacitance contribution, thereby creating a shoulder portion of capacitance. As shown in FIG. 5, the lower end of the first insulated marker 562 is located at a distance away from a free end of the electrode which corresponds to level L1, thereby exposing the most distal free end of the electrode.

When a diaper incorporating the graduated electrodes of FIG. 5 is wetted gradually and incrementally from levels L1 to L4, with level L4 being the marker at the highest vertical location during use, the characteristic capacitance values between the first and second electrodes due to the incremental urine soaking will change in the manner as shown in FIG. 5A and comprises characteristic shoulder regions 180. The shoulder regions are present because of the extra insulation on the electrode which means that there is no or minimum increment in capacitance output with the wetness level increase while in the insulation covered, or shoulder, region. On the other hand, capacitance output value will be incremental, in a substantially linear manner, when the wetness level increases in the non-covered electrode region. The characteristic shoulder regions of capacitance would provide useful information that a discrete, predefined, level has been reached without requiring precise capacitance calibration or pre-calibration.

While the markers are only present in the groin region 536 in this example, it will be appreciated without loss of generality that the markers are also provided on the hip region 532 and vice versa to facilitate a more intelligent diaper.

In addition to providing information on the degree or extent of wetness of the diaper, a diaper incorporating the electrodes of the present invention can also be used to provide wetness location information.

Figure 6:
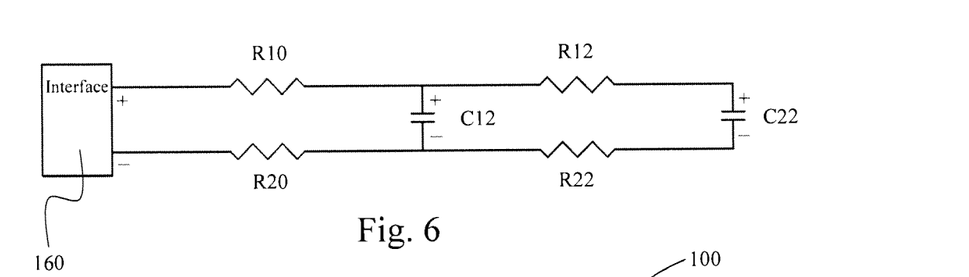
FIGS. 6 and 6A are respectively schematic diagrams depicting a diaper and a simplified equivalent circuit corresponding to the different regions of the diaper.
Figure 6A:
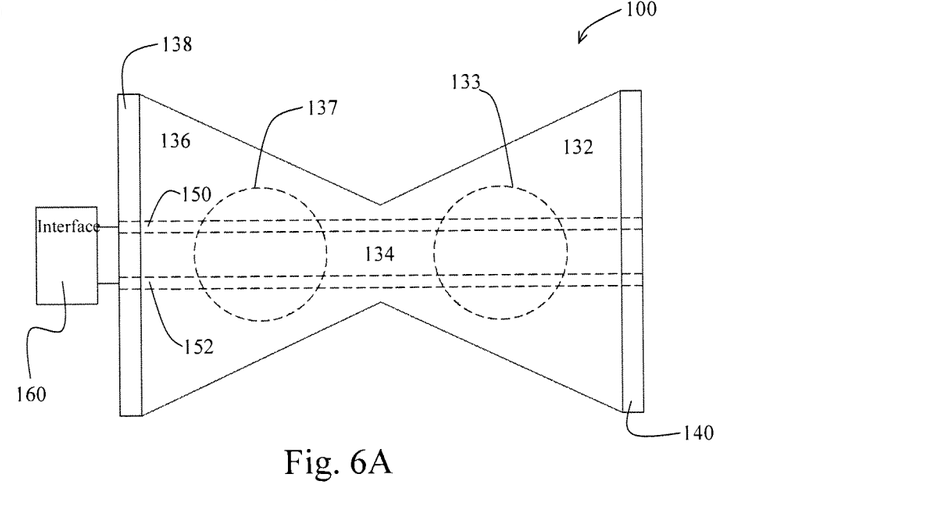

FIG. 6 is a schematic circuit diagram depicting a simplified equivalent circuit diagram of the diaper 100 of FIG. 1 above, with urine wetted patches depicted in FIG. 6A. As depicted in FIG. 6A, there are two wetted patches, namely, a first wetted patch 137 at the groin portion 136 at the front and a second wetted portion 133 at the hip portion 132 at the rear side. In the simplified equivalent circuit diagram, the electrodes are represented as a distributed circuit having distributed resistance along the electrodes and distributed capacitance between the electrodes. In a simplified representation for illustration purpose, the first electrode 150 is represented by a first resistive portion R10 and a second resistive portion R12 which are serially connected. The second electrode 152 is represented by a first resistive R20 and a second resistive portion R22 which are serially connected. The distributed capacitance is represented by a first capacitive element C12 in the first wetted patch 137 which is connected to R10, R12, R20 and R22, and a second capacitive element C22 in the second wetted patch 133 which is connected only to R12 and R22.

In the equivalent circuit diagram of FIG. 6, the resistive elements R10, R20 and the capacitive elements C12 are collectively representative of the total impedance of the wetted groin region 136 while the resistive elements R10, R12, R20, R22 and the capacitive element C22 are collectively representative of the total impedance of the wetted hip portion 132. It will be appreciated that the value of the capacitive elements C12 and C22 would be negligible until the hip and groin regions 132, 136 of the absorbent layer 126 are urine wetted respectively.

When the groin portion 136 is wetted, the total impedance measured across the electrodes 150, 152 would be R10+R20+C12. When the hip portion 132 are wetted, the total impedance measured across the electrodes 150, 152 would be R10+R12+R20+R22+C22. When both the hip portion 132 and the groin portion 136 are wetted, the total impedance measured across the electrodes 150, 152 would be R10+R12+R20+R22+C12+C22. In order to ascertain the wetted location or locations, the resistive components across the electrodes 150, 152 are measured. In order to determine the capacitive value, a constant current is applied and the voltage rising time or rate of voltage change is measured to determine the capacitive value across the electrodes 150, 152. By resolving the capacitive and resistive values across the electrodes with reference to the above relationship, the location of wetness can be determined.

In an example to determine the extent of wetness of the diaper 100 of FIG. 1, the sum of the distributed resistance R10 and R20 shown in the equivalent distributed circuit values FIG. 6 is 25 kΩ, the sum of R12 and R22 is 75 kΩ, and the capacitance of each of C12 and C22 is 100 µF. A constant current of 1 µA is applied by an external wetness detection device 160 to the contact terminals at the waist end 138 of the electrodes. By measuring the steady state voltage drop across the contact terminals, the resistance value can be obtained, and this resistance value will vary according to the total area of the wetted patches as described above. On the other hand, the total capacitance value of the wetted patches can be obtained by measuring the rate of voltage change which is inversely proportional to the capacitance value. By comparing the measured resistance and capacitance values according to the combination above, the area and location of wetness can be obtained.

Figure 7:
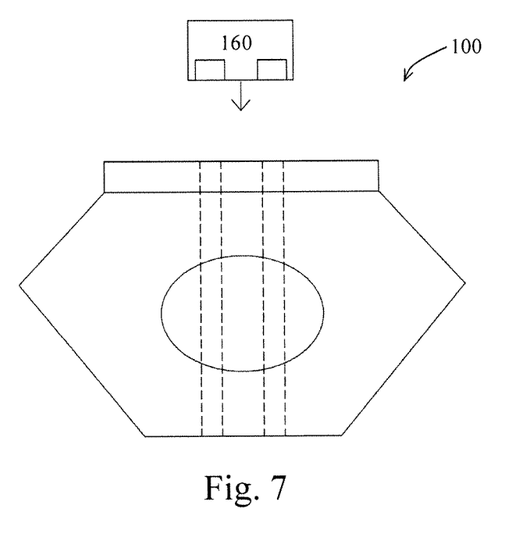
FIGS. 7 and 7A are schematic diagrams depicting use of a diaper with a wetness evaluation circuitry and a block diagram of an exemplary wetness evaluation circuitry.
Figure 7A:
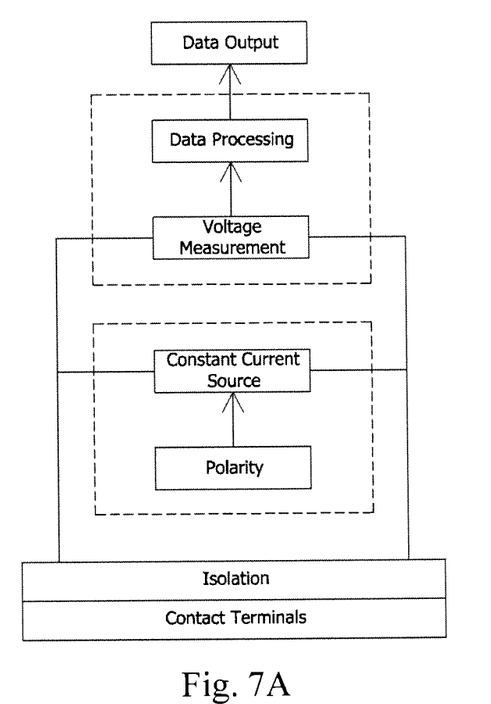

In use, a diaper is worn by a user with the output terminals of the electrodes connected to a wetness detection device 160 as shown in FIG. 7A. The wetness detection device 160 is suitable for use with the diaper of FIG. 7 and a schematic block diagram of the components of the wetness detection device 160 is shown in FIG. 7A. The example wetness detection device 160 comprises contact terminals for making electrical connection with the electrodes on the diaper, a processing circuitry, and an isolation circuit adapted to electrically isolate the electrode from the processing circuitry. The processing circuitry comprises a constant current source, a polarity setting circuitry, a voltage measurement circuitry adapted to detect the rate of voltage change in response to a constant current for capacitance measurement as well as to measure the steady state voltage with reference to the constant current to determine the resistive components as mentioned above, and a data processing circuitry to process the data due to the voltage measurements.

The contact making mechanism can be a pair of contact clips so that the wetness detection device can be detachable from the electrodes. In addition, the data output of the data processing circuitry can be wireless sent to a remote or centralized station such as a nurse station for efficient patient management.

It will be appreciated that the example of FIG. 5 can also be incorporated into a diaper and adapted for application in the manner as described above with reference to FIG. 6. With such a combination, location specific information can be more conveniently provided with less calculation by reference to the shoulder regions 180 of FIG. 5A since the identity of the plurality of shoulder regions can be easily determined.

Figure 8:
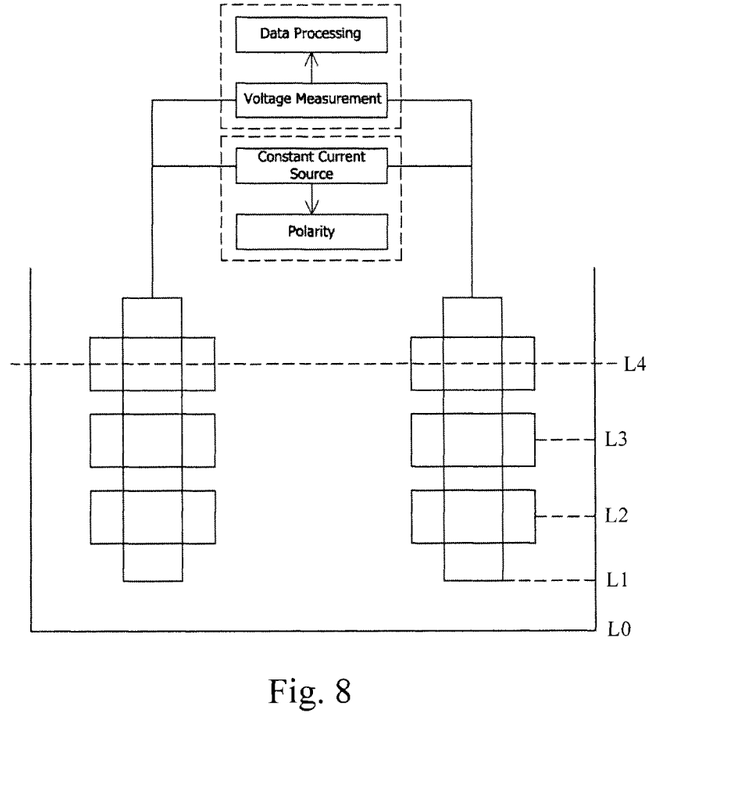
FIG. 8 is a schematic diagram of a wetness level detection device according to the present disclosure.

While the wetness detection arrangements above have been described with reference to diapers as examples, it will be appreciated that the wetness detection arrangements can be used in other applications. For example, the wetness detection arrangement comprising discrete markers can be used for electrolyte level detection as depicted in FIG. 8, and can be applied in appliances such as kettle, boiler, coffee machine, washing machine or other apparatus which require water or electrolyte level measurement.

While the above has been described with reference to diapers, it will be appreciated that the wetness sensing arrangements can be used in or with other wearable articles such as diving suits and work or protective clothing.

Diaper 100
Flexible diaper body 120
Inner layer 122
Outer layer 124
Absorbent layer 126
Inner surface 130
Hip region 132
Second wetted patch 133
Crotch portion 134
Groin region 136
First wetted patch 137
Front waist mount portion 138,
Rear waist mount portion 140
First electrode 150
Second electrode 152
Shoulder region 180
Third electrode 454,
Fourth electrode 456
Position markers 562, 564, 566

The invention claimed is:

1. A wearable article for wearing by a user comprising wetness sensing electrodes, wherein the wetness sensing electrodes are to be in contact with a wetting electrolytic liquid during normal use when the wearable article is wetted by the electrolytic liquid, and to operate as a capacitor upon application of a direct current at contact terminals of the wetness sensing electrodes when so wetted to facilitate capacitance measurement through the wetness sensing electrodes whereby wetness information of the wearable article is provided.

2. A wearable article according to claim 1, wherein the wetness sensing electrodes are adapted to operate as an electrolytic capacitor or an electrochemical capacitor upon application of a direct current when the wearable article is wetted by an electrolytic liquid such as urine during normal use, the applied direct current being below a threshold which will cause electrolysis of the electrolytic liquid.

3. A wearable article according to claim 2, wherein the wetness sensing electrodes comprises a first elongate electrode and a second elongate electrode, the second elongate electrode extending alongside the first elongate electrode.

4. A wearable article according to claim 3, wherein the wetness sensing electrodes are printed of carbonized ink.

5. A wearable article according to claim 1, wherein the capacitance measured through the wetness sensing electrodes upon application of the direct current is more than 1 microfarad (μF), and up to 10 μF or 100 μF when the wearable article is urine wetted during normal use.

6. A wearable article according to claim 1, where the wetness sensing electrodes is made of a material selected from a group consisting of pure carbon, activated carbon, carbon composite, carbon fiber composite, graphite, graphene, carbon nano-tube, carbon nano-fibre, carbonized ink, conductive rubber, metal oxides, aqueous synthetic substances, metal composite, or conductive polymers.

7. A wearable article according to claim 1, wherein at least one of the wetness sensing electrodes comprises a strip metal electrode which is covered with an insulating metal oxide of a high dielectric constant, and wherein the capacitance between the electrodes is determined by the wetted surface area of the electrode which is covered with the insulating metal oxide, the thickness and dielectric constant of the insulating oxide.

8. A wearable article according to claim 7, wherein the strip metal electrode comprises an aluminum electrode covered with aluminum oxide as an insulating dielectric layer, or a tantalum electrode covered with tantalum oxide as an insulating dielectric layer, the insulating oxide layer having a thickness of more than 2 nanometers.

9. A wearable article according to claim 1, wherein the wetness sensing electrodes comprises markers which are provided to output information on specific locations of wetness.

10. A wearable article according to claim 1, wherein the wearable article is a diaper having an absorbent layer and a liquid non-permeable outer layer, wherein the wetness sensing electrodes are in direct contact with the absorbent layer such that the wetness sensing electrodes are immersed in a wetting liquid when the absorbent layer is wetted by the wetting electrolytic liquid during normal use.

11. A diaper according to claim 10, wherein each one of the wetness sensing electrodes has a length of more than 250 mm.

12. A diaper according to claim 11, wherein each one of the wetness sensing electrodes has a width of more than 2 mm.

13. A diaper according to claim 10, wherein a first side of the absorbent layer is adapted to face the skin of a user during use, and a second side of the absorbent layer is adapted to face away from the user during use; and wherein the wetness sensing electrodes are disposed on the same side of the absorbent layer.

14. A diaper according to claim 10, wherein a first surface of the absorbent layer is adapted to face the skin of a user during use, and a second surface of the absorbent layer is adapted to face away from the user during use; and wherein the absorbent layer is intermediate the wetness sensing electrodes.

15. A diaper according to claim 10, wherein the wetness sensing electrodes extend between longitudinal ends of the diaper and traverse a hip region, a groin region and a crotch regions, and wherein the wetness sensing electrodes are adapted to output region specific wetness information location for display.

16. A wetness detection device for evaluating wetness of a wearable article, the wearable article comprising wetness sensing electrodes which are to be in contact with a wetting electrolytic liquid during normal use, wherein the device comprises a direct current source and a processor which measures capacitance of the wetness sensing electrodes when the electrolytic liquid is in contact with the wetness sensing electrodes by applying a direct current to the electrodes, and to process measured capacitance values to determine the wetness state.

17. A wetness detection device according to claim 16, wherein the direct current source comprises a constant current source.

18. A wetness detection device according to claim 16, wherein the device comprises polarity setting circuitry to reverse polarity of direct current applied to the electrodes and to further measure capacitance under reversed polarity.

19. A wetness detection device according to claim 16, wherein the device further comprises means for measuring resistance or variation on resistance of the wetness sensing electrodes to provide location specific wetness information.

20. An electrolytic level detecting device comprising a first electrode, a second electrode and detection circuitry, wherein the first and second electrodes are adapted to be immersed in an electrolyte the level of which is to be detected, and the detection device is adapted to facilitate measurement of capacitance between the first and second electrodes to provide level information by direct current; wherein at least one discrete wetness level marker is formed on at least one of the electrodes to provide a discrete indication on the level of the electrolyte; and wherein the level marker comprises a capacitance mask which operate to generate a shoulder region in the capacitive characteristic of the electrolyte immersed electrodes.

* * * * *